(12) United States Patent
Pirutko et al.

(10) Patent No.: US 7,081,552 B2
(45) Date of Patent: Jul. 25, 2006

(54) CATALYSTS FOR CYCLOALKANES OXIDATION AND DECOMPOSITION OF CYCLOALKYL HYDROPEROXIDE

(75) Inventors: Larisa V. Pirutko, Novosibirsk (RU); Alexander S. Kharitonov, Novosibirsk (RU); Mikhail I. Khramov, Pensacola, FL (US); Anthony K. Uriarte, Pensacola, FL (US)

(73) Assignee: Solutia Inc., St. Louis, MO (US)

( * ) Notice: Subject to any disclaimer, the term of this patent is extended or adjusted under 35 U.S.C. 154(b) by 0 days.

(21) Appl. No.: 10/920,021

(22) Filed: Aug. 17, 2004

(65) Prior Publication Data

US 2006/0041172 A1    Feb. 23, 2006

(51) Int. Cl.
*C07C 45/27* (2006.01)
*C07C 35/08* (2006.01)

(52) U.S. Cl. .................. 568/354; 568/357; 568/836

(58) Field of Classification Search ............... 568/354, 568/357, 836
See application file for complete search history.

(56) References Cited

U.S. PATENT DOCUMENTS

| | | | |
|---|---|---|---|
| 5,767,320 A | 6/1998 | Raja et al. | 568/369 |
| 5,827,406 A * | 10/1998 | Frei et al. | 204/157.15 |
| 5,859,301 A | 1/1999 | Kragten et al. | 568/342 |
| 6,150,562 A | 11/2000 | Frei et al. | 568/400 |
| 6,160,183 A | 12/2000 | Druliner et al. | 568/360 |
| 6,284,927 B1 | 9/2001 | Druliner et al. | 568/342 |
| 6,806,390 B1 * | 10/2004 | Herron et al. | 568/342 |

FOREIGN PATENT DOCUMENTS

| | | |
|---|---|---|
| WO | WO 98/00413 | 1/1998 |
| WO | WO 99/40055 | 8/1999 |
| WO | WO 00/53550 | 9/2000 |

OTHER PUBLICATIONS

Lu et al. A highly efficient catalyst Au/MCM-41 for selective oxidation of cyclohexane using oxygen. Catalysis Letters, 2004, vol. 97, (3-4), p. 115-118.*
World Gold Council, *Patents Relating to Gold Catalysis 2001—1991*, 9 sheets (front and back), published via Internet (2001) http://www.gold.org/discovery/sci_indu/gold_catalysis/pdf/Gold%20catalysis%20patents%WGC%20website.pdf.
Abstract, The Chinese Academy of Sciences, Journal of Natural Gas Chemistry, *Cyclohexane oxidation catalyzed by titanium Silicalite (S-1) with hydrogen peroxide*, vol. 10 No. 4, (2001).
Abstract, Journal of the Brazilian Chemical Society, *Copper containing silicates as catalysts for liquid phase cyclohexane oxidation*.
Fan, Fengwen, et al., *Environmentally Benign Oxidation of cyclohexane and Alkenes with Air over Zeolite-Encapsulated Au Catalysts*, 1 sheet (front and back), 4th World Congress on Oxidation Catalysis, Sep. 16-21, 2001, Berlin/Potsdam, Germany.
Schuchardt, Ulf, et al., *Cycleohexane oxidation continues to be a challenge*, Applied Catalysis A: Generall 211, pp. 1-17, 2001.

* cited by examiner

*Primary Examiner*—Sikarl A. Witherspoon
(74) *Attorney, Agent, or Firm*—Jones, Tullar & Cooper, P.C.; John P. Foryt

(57) ABSTRACT

A cyclic ketone/alcohol mixture is prepared by catalytic oxidation of the corresponding cycloalkane or catalytic decomposition of the corresponding cycloalkyl hydroperoxide. Gold supported on a porous crystalline silicate containing less than about 2 wt. % aluminum or a crystalline phosphate is used as a catalyst. The support material optionally contains one or more heteroatoms.

27 Claims, No Drawings

CATALYSTS FOR CYCLOALKANES OXIDATION AND DECOMPOSITION OF CYCLOALKYL HYDROPEROXIDE

FIELD OF THE INVENTION

The present invention is directed to catalytic oxidation of cycloalkanes and to catalytic decomposition of cycloalkyl hydroperoxides to form mixtures containing the corresponding ketones and alcohols.

BACKGROUND OF THE INVENTION

Several different processes have been used for the oxidation of cyclohexane into a product mixture containing cyclohexanone and cyclohexanol. Such product mixture is commonly referred to as a KA (ketone/alcohol) mixture. The KA mixture can be readily oxidized to produce adipic acid, which is an important reactant in processes for preparing certain condensation polymers, notably polyamides. Given the large quantities of adipic acid consumed in these and other processes, there is a need for cost-effective processes for producing adipic acid and its precursors.

One technique presently used for cyclohexane oxidation employs metaboric acid as a catalyst. Although metaboric acid is a somewhat effective oxidation catalyst, certain drawbacks are associated with its use. A principal drawback is the need for catalyst recovery, which typically involves hydrolysis of the reaction mixture, aqueous and organic phase separation, and dehydration of boric acid. These steps introduce considerable complexity and expense into the overall process.

Organic cobalt salts, such as cobalt octanoate, have been widely used for oxidizing cyclohexane into KA mixtures. Various homogenous metal catalysts also have been proposed for oxidizing cycloalkanes, such as salts of chromium, iron, and manganese, with varying results in terms of cyclohexane conversion and ketone/alcohol selectivities.

Two-stage processes also have been used for cycloalkane oxidation. In a first stage of one typical two-stage process, cyclohexane is oxidized to form a reaction mixture containing cyclohexyl hydroperoxide (CHHP). In a second stage, CHHP is decomposed, with or without use of a catalyst, to form a KA mixture. An example of a two-stage process is described in U.S. Pat. No. 6,284,927 to Druliner et al., in which an alkyl or aromatic hydroperoxide is oxidized in the presence of a heterogeneous catalyst of Au, Ag, Cu or a sol-gel compound containing particular combinations of Fe, Ni, Cr, Co, Zr, Ta, Si, Mg, Nb, Al and Ti, wherein certain of these metals are combined with an oxide. Other catalysts that have been proposed for the second stage of two-stage oxidation processes include salts of manganese, iron, cobalt, nickel, and copper.

WO 00/53550 and companion U.S. Pat. No. 6,160,183 to Druliner et al. describe a heterogeneous catalyst for so-called direct oxidation of cycloalkanes to form a KA mixture. The catalysts described include gold, gold sol-gel compounds, and sol-gel compounds containing particular combinations of Cr, Co, Zr, Ta, Si, Mg, Nb, Al and Ti, wherein certain of these metals are combined with an oxide.

Fan et al., "Environmentally Benign Oxidations of Cyclohexane and Alkenes with Air Over Zeolite-encapsulated Au Catalysts," Lanzhou Institute of Chemical Physics, Chinese Academy of Sciences, discloses catalysts for the oxidation of cyclohexane and alkenes. Au/NaY is said to yield high turnover frequency and product selectivities when used as an oxidation catalyst for cyclohexane.

There remains a need for cost-effective methods for oxidizing cycloalkanes to KA mixtures, particularly methods employing catalysts that yield high cycloalkane conversions, high ketone and alcohol selectivities, and relatively low cycloalkyl hydroperoxide concentrations.

SUMMARY OF THE INVENTION

The present invention is directed to a method of oxidizing a cycloalkane in a reaction mixture to form a product mixture containing a corresponding alcohol and ketone. The method comprises contacting the reaction mixture with a source of oxygen in the presence of a catalytic effective amount of gold supported on a porous crystalline silicate or phosphate support.

The present invention is also directed to a method for catalytic decomposition of a cycloalkyl hydroperoxide to form a product mixture containing a corresponding alcohol and ketone. The method comprises contacting the reaction mixture containing cycloalkyl hydroperoxide with a catalytic effective amount of gold supported on a porous crystalline silicate containing less than about 2 wt % aluminum or a crystalline phosphate support.

Porous crystalline silicates optionally may contain one and more heteroatoms and can be described by the general formula: $(El_2O_n)_x SiO_2$, where $x=0-0.13$, El is at least one element of Periods 2, 3, 4 and 5 of the periodic system except for aluminum and n is valence of the element El.

Porous crystalline phosphates optionally may contain one and more heteroatoms and can be described by the general formula: $(El_2O_n)_x(Al_2O_3)_y P_2O_5$, where $x \leq 0.27$, $y \leq 1.0$, El is at least one element of Periods 2, 3, 4 and 5 of the periodic system and n is the valence of the element El.

The supported gold catalysts of the present invention used for cycloalkyl oxidation have been found to yield product mixtures characterized by high cycloalkane conversions, high ketone and alcohol selectivities, and relatively low cycloalkyl hydroperoxide concentrations. These catalysts thus exhibit exceptional performance in cycloalkane oxidation. In addition, the insoluble heterogeneous catalyst provides a significantly simplified operation compared to the use of boric acid as catalyst. The insoluble heterogeneous catalyst also can be used in any other form known to those skilled in the art, such as slurry, in a catalytic basket, fixed bed, supported on a grid or honeycomb structure and the like. For example, catalyst recovery may be unnecessary if a catalyst basket or the like is used. If the catalyst is used as slurry it can be easily recovered by filtration, centrifugation, or any conventional means.

The supported gold catalysts of the present invention used for cycloalkyl hydroperoxide decomposition have been found to yield product mixtures characterized by high activity in cycloalkyl hydroperoxide decomposition, and high ketone and alcohol selectivities. The supported gold catalysts for cycloalkyl hydroperoxide decomposition can be used in the same form as the supported gold catalyst for cycloalkyl oxidation described above.

DETAILED DESCRIPTION OF THE INVENTION

The present invention is directed to methods for catalytic oxidation of cycloalkanes. The term "cycloalkane", as used herein, refers to saturated cyclic hydrocarbons having from 3 to about 10 carbon atoms, more usually from about 5 to about 8 carbon atoms. Non-limiting examples of cycloalkanes include cyclopentane, cyclohexane, cycloheptane, and cyclooctane.

The present invention is also directed to methods for catalytic decomposition of cycloalkyl hydroperoxides. The term "cycloalkyl hydroperoxide", as used herein, refers to hydroperoxides of saturated cyclic hydrocarbons having from 3 to about 10 carbon atoms, more usually from about 5 to about 8 carbon atoms. Non-limiting examples of cycloalkyls include cyclopentyl, cyclohexyl, cycloheptyl, and cyclooctyl hydroperoxides.

The catalyst of the present invention comprises gold supported on a porous crystalline silicate containing less than about 2 wt % aluminum or a crystalline phosphate support. Gold can be supplied in any suitable form. For example, it can be deposited onto the support by impregnation, precipitation, deposition-precipitation, ion-exchange, anion or cation adsorption from solutions, and vapor phase deposition. In addition, gold containing catalysts can be prepared by introducing the source of gold at the stage of hydrothermal synthesis of the support material. When using the above-mentioned and other possible methods, the amount of introduced gold is varied in a wide range up to about 10 wt %. The catalyst typically contains ultra fine sized gold particles from about 3 to about 15 nm in diameter.

The porous crystalline silicate can have a variety of structures, non-limiting examples of which include BEA, FAU, MFI, MEL, MOR, MTW, MTT, MCM-22, MCM-41, MCM-48, and NU-1. A fraction of the silicon in the crystalline silicate may be isomorphically or non-isomorphically replaced by one or more heteroatoms chosen from a series of B, Be, Ga, In, Ge, Sn, Ti, Zr, Hf, V, Cr, Mn, Fe, Co, P, Mo, and W or any other element of Periods 2, 3, 4 and 5 of the periodic system except for aluminum. The aluminum content in the porous crystalline silicate should be below about 2 wt. %, preferably below about 1 wt. %. If the replacement is isomorphic and the valence of the replacing element is not equal to the valence of silicon, a corresponding crystalline silicate may contain in cationic positions hydrogen cations, and/or cations of alkaline ($Li^+$, $Na^+$, $K^+$, etc.) and/or alkaline-earth metal ($Mg^{2+}$, $Ca^{2+}$, $Sr^{2+}$, etc.), and/or cations and/or oxycations of any transition metal (e.g., $Cu^+$, $Zn^{2+}$, $VO^+$, $FeO^+$, etc.).

Porous crystalline phosphate supports also can be used for preparation of gold containing catalysts, which provide optimal catalyst performance in cycloalkane oxidation and cycloalkyl hydroperoxide decomposition. The porous crystalline phosphate support can have a variety of structures, non-limiting examples of which include AFI, AEL, AFO, AFR, AFS, AFT, AFY, ATN, ATO, ATS, ATT, ATV, AWW. A fraction of the phosphorus in the crystalline silicate can be isomorphically or non-isomorphically replaced by one or more heteroatoms chosen from a series of Al, Si, B, Be, Ga, In, Ge, Sn, Ti, Zr, Hf, V, Cr, Mn, Fe, Co, Mo, W.

A dealuminated zeolite support also can be used as a crystalline porous silicate for preparation of gold containing catalysts, which provide optimal catalyst performance in cycloalkane oxidation and cycloalkyl hydroperoxide decomposition. The dealuminated zeolite support can have a variety of structures, non-limiting examples of which include AFI, AEL, AFO, AFR, AFS, AFT, AFY, ATN, ATO, ATS, ATT, ATV, and AWW. The degree of dealumination should be such that the residual aluminum content is below 1 wt. % and preferably below 0.1 wt. %.

Preferred catalysts of the present invention provide selectivities of about 90% at cyclohexane conversions up to about 6–7%. In the absence of air, the catalyst decomposes cyclohexyl hydroperoxide (CHHP) to cyclohexanol and cyclohexanone with the selectivity close to 100%. Preferred catalysts according to the present invention demonstrate a significantly higher stability of their performance than the known gold containing catalysts.

The crystalline structure of a porous crystalline silicate or phosphate material is formed by tetrahedral fragments (e.g., $[SiO_4]^{4-}$, $[PO_4]^{3+}$) combined by their common vertices into a three-dimensional framework with cavities and channels. The above methods for preparing gold containing catalysts provide arrangement of ultra-fine sized gold particles in the channels and cavities of the micropore space of a support, or in the pore entrances of the external surface of the crystals. Such arrangement of gold particles prevents their sintering at thermal treatment of the catalyst and increases the operation stability of the catalyst.

Porous crystalline silicate or phosphate supports can be prepared in accordance with methods well known to persons skilled in the art (J. Weitkamp, L. Puppe (Eds) Catalysis and Zeolites. Fundamentals and Applications. Springer, p. 1–52.). For example, porous crystalline silicates can be prepared by the following method. A mixture consisting of a source of silicon, a source of $El^{n+}$ (if it is needed), an alkali, organic surfactants and, in some cases, a crystallization seed, is homogenized and then placed into an autoclave, wherein under hydrothermal conditions it is kept for 10 hours to 30 days at a temperature within a range of from 80° C. to 200° C. Prior to use as a support, the solid product may be calcined at a temperature within the range from 450° C. to 800° C. Varying the chemical composition of the mixture, temperature and time of the hydrothermal synthesis, one may produce a silicate of desired structure. If an alumosilicate having zeolite structure is used as a precursor for preparation of a porous crystalline silicate according to the present invention, its aluminum content needs to be reduced to below about 2 wt. % aluminum, preferably below about 1 wt. %. This can be achieved using methods well known to persons skilled in the art, for example, by treating the support at an elevated temperature with a gas containing steam.

In addition, the gold containing catalyst may be subjected to post-synthesis treatment including but not limited to washing with acids or chelating agents, treatment with a reducing or oxidizing or inert gas, or mixtures of steam with reducing or oxidizing or inert gas.

Porous crystalline phosphates can be prepared using any known method (J. Weitkamp, L. Puppe (Eds) Catalysis and Zeolites. Fundamentals and Applications. Springer, p. 53–80). For example, a mixture consisting of a source of phosphorus, a source of aluminum and/or $El^{n+}$ (if it is needed), an alkali, organic surfactants and, in some cases, a crystallization seed, is homogenized and then placed into an autoclave, wherein under hydrothermal conditions it is kept for 10 hours to 30 days at a temperature within a range of from 80° C. to 200° C. Prior to use as a support, the solid product may be calcined at a temperature within the range from 450° C. to 800° C. for removal of organic inclusions. Varying the source of phosphorus and aluminum, the nature of organic surfactant, temperature and time of hydrothermal synthesis, one may produce a crystalline phosphate of a given structure.

In the practice of the invention, the catalysts can be contacted with a cycloalkane, such as cyclohexane, by formulation into a catalyst bed, which is arranged to provide intimate contact between the catalyst and reactants. Alternatively, catalysts can be slurried with reaction mixtures using techniques known in the art. The process of the invention is suitable for either batch or continuous cycloalkane oxidation. These processes can be performed under a wide variety of conditions, as will be apparent to persons of ordinary skill in the art.

Suitable reaction temperatures for the processes of the invention typically range from about 130 to about 200° C., more usually from about 150 to about 180° C. Reaction pressures often range from about 69 kPa to about 2760 kPa (53–400 psia), more usually from about 552 kPa to about 1380 kPa (80–200 psia) (to keep in liquid phase). Cycloalkane reactor residence time generally varies in inverse relation to reaction temperature, and is typically less than 120 min.

The source of oxygen used in the oxidation may be molecular oxygen itself but is conveniently air or other mixtures of nitrogen and oxygen with a higher or lower proportion of oxygen than that of air, obtained, for example, by mixing oxygen or nitrogen with air. However, air is preferred. The time of contacting the air with the liquid phase in the reactor varies from 0.05 to 5 minutes, more usually from about 0.2 to about 1.5 minutes.

In addition to being used in the cycloalkane oxidation reactor, the catalyst also can be used in a separate reactor to assist the conversion of cycloalkane hydroperoxide, which forms during oxidation, to cycloalkanol and cycloalkanone. In this case the reaction mixture produced during the oxidation of a cycloalkane with molecular oxygen is brought into contact with a catalyst at a temperature of 50 to 200° C., preferably 100 to 170° C. The pressure is maintained at a sufficient level to keep the cycloalkane in the liquid phase at the process temperature. Typically the pressure is maintained in the range of 100 to 1380 kPa (15–200 psig), preferably 172 to 830 kPa (25–120 psig). The time required to convert cycloalkyl hydroperoxide to cycloalkanol and cycloalkanone depends on the catalyst, reactant to catalyst ratio, temperature and other parameters. In the preferred embodiments of the present invention the time usually does not exceed 10 seconds.

The following examples are provided for illustrative purposes only and should not be regarded as limiting the invention.

EXAMPLE 1

Preparation of Silicalite-1 Support

Silicalite-1 was prepared as described in Flanigen E. M., Bennett J. M., Grose R. W., Cohen J. P., Patton R. L., Kirchner R. M., Smith J. V. (1978) Nature 271, 512. Silica sol (36 g) containing 40% $SiO_2$ was added to 220 ml 0.1 M tetrapropylammonium hydroxide solution. The mixture was agitated for 30 minutes, and 4 ml of 10 M NaOH aqueous solution was added to it dropwise. The resulting mixture was agitated for 1 hour at ambient temperature and kept for 72 hours at 170° C. The precipitate was filtered, washed with distilled water and dried for 24 hours at 100 deg.C. XRD analysis confirmed the MFI structure of the obtained product.

Preparation of Au/Silicalite-1 Catalyst

This example illustrates preparation of a gold containing catalyst using a silicalite-1, a porous crystalline silicate, as a support. Silicalite-1 (3 g) was suspended in 50 ml water, and 7.9 ml of 0.05 M $HAuCl_4$ was added dropwise to this suspension. The pH of the resulting slurry was adjusted to 7 with 6% aqueous ammonia; the slurry was agitated for additional 2 hours. The precipitate was filtered, dried for 10 hours at 100° C. and calcined 2 hours at 200° C.

EXAMPLE 2

This example illustrates preparation of a gold catalyst using a titanosilicate TS-1 of MFI structure having the following composition $(TiO_2)_{0.025}(SiO_2)$. The catalyst was prepared according to Example 1, wherein crystalline titanium silicate TS-1 was used as support.

Preparation of TS-1 Support

Tetraethylorthosilicate (91 g) was placed in a glass flask under inert atmosphere. Tetraethyltitanate (3 g) was added under stirring. Tetrapropylammonium hydroxide (25% aqueous solution, 160 g) was added and the mixture was stirred 1 hour at ambient temperature and 5 hours at 80–90° C. After that time, the mixture was transferred into an autoclave and kept for 10 days at 175° C. The product was cooled, filtered and washed with distilled water. Organic template was removed by calcination for 3 hours at 550° C. X-ray diffraction analysis showed that the product was MFI structure.

EXAMPLE 3

This example illustrates preparation of a gold catalyst using a borosilicate of MFI structure having the following composition $(B_2O_3)_{0.0083}(SiO_2)$. The catalyst was prepared according to Example 1, wherein borosilicate was used as support.

Preparation of Borosilicate Support

Tetrapropylammonium hydroxide (25% aqueous solution, 61 g) was placed in a glass flask under an inert atmosphere. Boric acid (9.3 g) was added under stirring. Tetraethylorthosilicate (93.75 g) was added and the mixture was gradually heated to 60° C. and kept at this temperature under constant stirring for 12 hours. After that time, KOH (0.09 g) and distilled water were added to make the overall volume 150 ml. The mixture was transferred into an autoclave and kept for 12 days at 145° C. The product was cooled, filtered, washed with distilled water, and dried at 120° C. Organic template was removed by calcination at 750° C. X-ray diffraction analysis showed that the product had MFI structure. The material is referred to as B-ZSM-5 below.

EXAMPLE 4

This example illustrates preparation of a gold catalyst on a dealuminated alumosilicate $(Na_2O)_{0.0025}(Al_2O_3)_{0.023}SiO_2$ of FAU structure. This sample contained 7 times less aluminum than a typical Y zeolite. The catalyst was prepared according to Example 1, wherein 0.03 M aqueous $HAuCl_4$ solution was used as a source of gold. The support was prepared as described in Kerr G. T., J. Phys. Chem 71 (1967) 4155.

EXAMPLE 5

This example illustrates preparation of a gold catalyst on a crystalline alumophosphate with ATS structure having the following composition $Al_2O_3.P_2O_5$. The catalyst was prepared according to Example 1, wherein alumophosphate was used as support. The support was prepared as described in Bennet J. M., Richardson J. M., Pluth J. J., Smith J. V. (1987) Zeolites 7, 160.

EXAMPLE 6

This example illustrates preparation of a gold catalyst using a dealuminated alumosilicate $(Na_2O)_{0.00007}(Al_2O_3)_{0.0086}SiO_2$ of MFI structure. The catalyst was prepared according to Example 1, wherein crystalline porous silicate was used as support. The support was prepared as described in Argauer R. J., Landolt G. R. (1972) U.S. Pat. No. 3,702,886. To remove the aluminum from the alumosilicate lattice and reduce the acidity, the support was additionally treated with steam at 650° C. for 2 hours prior to deposition of gold.

EXAMPLE 7

This example illustrates preparation of a gold catalyst using an alumosilicate $(Na_2O)_{0.0086}(Al_2O_3)_{0.0086}SiO_2$ of MFI structure. The catalyst was prepared according to Example 1, wherein alumosilicate was used as support. The support was prepared as described in Argauer R. J., Landolt G. R. (1972) U.S. Pat. No. 3,702,886. To remove aluminum from the alumosilicate lattice and reduce the acidity, the support was additionally treated with steam at 650° C. for 2 hours prior to deposition of gold.

EXAMPLES 8–19

Examples 8–19 illustrate using the catalysts of Examples 1–5 for the oxidation of cyclohexane.

Each of the catalysts according to Examples 1–5 (0.8–0.9 g) was loaded into a 300 ml Parr pressure reactor containing cyclohexane (160 g) and cyclohexanone (0 or 0.70 g). The reactor was purged for 20 minutes with helium (300 cc/min at atmospheric pressure) and, after that, pressurized with helium to 130–140 psig. The contents of the reactor were heated to 150° C. or 170° C., helium flow was shut down, and air was fed to the reactor at the rate of 300 cc/min until the desired cyclohexane conversion was achieved. The results of the tests are indicated in Table 1.

COMPARATIVE EXAMPLES 20–28

These comparative examples illustrate oxidizing cyclohexane without a catalyst. Cyclohexane (160 g) and cyclohexanone (0 or 0.70 g) were loaded into a 300 ml Parr pressure reactor. The reactor was purged for 20 minutes with 300 cc/min helium at atmospheric pressure and, after that, pressurized with helium to 130–140 psig. The contents of the reactor were heated to 150° C. or 170° C., helium flow was shut down, and air was fed to the reactor at the rate of 300 cc/min until the desired cyclohexane conversion was achieved. The results of the tests are indicated in Table 1.

COMPARATIVE EXAMPLE 29

This comparative example illustrates oxidizing cyclohexane using borosilicate B-ZSM-5 with MFI structure without gold as a catalyst.

Boron-containing ZSM-5 (B-ZSM-5) was prepared according to the first part of Example 3 (the catalyst did not contain gold). The catalyst was tested in cyclohexane oxidation as in Examples 8–19. The results of the test are shown in Table 1.

COMPARATIVE EXAMPLE 30

This comparative example illustrates oxidizing cyclohexane using porous crystalline silicate with MFI structure, silicalite-1, without gold as a catalyst.

Silicalite-1 was prepared according to the first part of Example 1; the catalyst did not contain gold. The silicalite was tested in cyclohexane oxidation as in Examples 8–19. The results of the test are shown in Table 1.

COMPARATIVE EXAMPLE 31

This comparative example illustrates oxidizing cyclohexane using titanosilicate TS-1 with MFI structure without gold as a catalyst.

Titanosilicate TS-1 was prepared according to the first part of Example 2 (the catalyst did not contain gold). The titanosilicate was tested in cyclohexane oxidation as in Examples 8–19. The results of the test are shown in Table 1.

COMPARATIVE EXAMPLE 32

This comparative example illustrates oxidizing cyclohexane using crystalline alumophosphate without gold as a catalyst.

Crystalline alumophosphate was prepared according to the Example 5 (the catalyst did not contain gold). The catalyst was tested in cyclohexane oxidation as in Examples 8–19. The results of the test are shown in Table 1.

COMPARATIVE EXAMPLE 33

This comparative example illustrates preparation of an Au on amorphous $SiO_2$ catalyst and using this catalyst in cyclohexane oxidation.

$Au/SiO_2$ catalyst was prepared using sol-gel method. Tetraethylorthosilicate (10.5 g) and 1.3 ml of 0.12 M solution $HAuCl_4$ were dissolved in ethanol, and dilute aqueous $NH_3$ solution was added until the mixture became turbid. The mixture was held for 15 hours; the precipitate was filtered, washed and dried. The catalyst was tested in cyclohexane oxidation as in Examples 8–19. The results of the test are indicated in Table 1.

COMPARATIVE EXAMPLE 34 y-$Al_2O_3$ (basic, Alpha Aesar, 5.984 g) was suspended in 117.3 g solution of 0.1% $AuCl_3$ in 0.5% HCl. The slurry was titrated with 9% $NH_3$ to pH 7.0. The agitation continued for 4 hours at ambient temperature. The slurry was filtered, and the precipitate was washed on a filter with 50 ml water, dried overnight at 110° C., and calcined 3 hours at 450° C. The catalyst, $Au/Al_2O_3$ was tested in cyclohexane oxidation as in Examples 8–19. The results of the test are indicated in Table 1.

COMPARATIVE EXAMPLE 35

This comparative example illustrates preparing a gold catalyst on NaY zeolite, an alumosilicate $(Na_2O)_{0.026}(Al_2O_3)_{0.15}SiO_2$ of FAU structure and using the catalyst in cyclohexane oxidation. The catalyst was prepared according to Example 1, wherein 0.03 M aqueous $HAuCl_4$ solution was used as a source of gold. The support was prepared as described in Breck D. W. U.S. Pat. No. 3,130,007 (1964).

The catalyst, Au/NaY was tested in cyclohexane oxidation as in Examples 8–19. The results of the test are indicated in Table 1.

Examples 36–39 illustrate using the catalysts of Examples 1, 4, 6 and 7 for CHHP decomposition.

The catalysts according to Examples 1, 4, 6 and 7 were tested in a fixed bed reactor, a metal tube (SS316) of internal diameter 4.5 mm. To prevent CHHP from reacting on metal walls of the reactor, the reactor was passivated by treating its surface with a $Na_4P_2O_7$ solution. The liquid feed material was passed through the catalyst bed using a syringe pump. The effluent from the reactor was collected in the collection vessel. The catalyst charge was 0.3 g. typically, the catalyst was charged into the reactor, and cyclohexane feed, 0.6 ml/min, was turned on. As cyclohexane displaced air, the pressure in the system gradually increased. After the pressure had reached the set point of 170 psig, the heating was applied to the reactor. Once the temperature in the catalyst bed reached the desired value, 160° C., the cyclohexane feed was stopped and the feed of the mixture containing cyclohexyl hydroperoxide, 8.8 mol/l, cyclohexanone, 1.2 mol/l, cyclohexanol, 2.6 mol/l and side products*, 1.1 mol/l, began. The time on stream was counted from this moment. The effluent from the reactor was sampled every 30 minutes. The samples were analyzed on a gas chromatograph. The catalysts were usually tested for 3 to 5 hours.

*Side products concentration is expressed in CHHP equivalent

The composition of the feed mixture changed as it passed through the catalyst. The CHHP concentration decreased, while the concentrations of cyclohexanol and cyclohexanone increased, which indicated the transformation CHHP to KA-oil. Averaged for the first 3 hours cyclohexyl hydroperoxide conversion and total selectivity for ketone and alcohol are indicated in Table 2.

Table 2 also shows the deactivation parameter of the catalysts, the ratio of CHHP conversion after 180 and 60 min on stream.

COMPARATIVE EXAMPLE 40

This comparative example illustrates CHHP decomposition without a catalyst. The reaction conditions are the same as in examples 36–39. The results of the test are shown in Table 2.

COMPARATIVE EXAMPLE 41

This comparative example illustrates CHHP decomposition using porous crystalline silicate with MFI structure, silicalite-1, without gold as a catalyst.

Silicalite-1 was prepared according to the first part of Example 1 (the catalyst did not contain gold). The catalyst was tested in CHHP decomposition as in Examples 36–39. The results of the test are shown in Table 2.

COMPARATIVE EXAMPLE 42

This comparative example illustrates CHHP decomposition using a dealuminated alumosilicate $(Na_2O)_{0.0086}(Al_2O_3)_{0.0086}SiO_2$ of MFI structure without gold as a catalyst.

The dealuminated alumosilicate $(Na_2O)_{0.0086}(Al_2O_3)_{0.0086}SiO_2$ was prepared as the support in Example 7 (the catalyst did not contain gold). The catalyst was tested in cyclohexane oxidation as in Examples 36–39. The results of the test are shown in Table 2.

COMPARATIVE EXAMPLE 43

This comparative example illustrates CHHP decomposition using a dealuminated alumosilicate $(Na_2O)_{0.00007}(Al_2O_3)_{0.0086}SiO_2$ of MFI structure without gold as a catalyst. This example is different from Example 42 in that the catalyst used in this example was converted to H-form and contained a small amount of sodium.

The alumosilicate $(Na_2O)_{0.00007}(Al_2O_3)_{0.00816}SiO_2$ was prepared as the support in Example 4 (the catalyst did not contain gold). The catalyst was tested in cyclohexane oxidation as in Examples 36–39. The results of the test are shown in Table 2.

COMPARATIVE EXAMPLE 44

This comparative example illustrates CHHP decomposition using a gold catalyst on zeolite NaY, an alumosilicate $(Na_2O)_{0.15}(Al_2O_3)_{0.15}SiO_2$ of FAU structure.

The catalyst was prepared according to Example 1, wherein 0.03 M aqueous $HAuCl_4$ solution was used as a source of gold. The support was prepared as described in Breck D. W. U.S. Pat. No. 3,130,007 (1964). The catalyst was tested in CHHP decomposition as in Examples 36–39. The results of the test are shown in Table 2.

COMPARATIVE EXAMPLE 45

This comparative example illustrates CHHP decomposition using a gold catalyst on zeolite NaY, an alumosilicate $(Na_2O)_{0.026}(Al_2O_3)_{0.15}SiO_2$ of FAU structure. This example is different from Example 44 in that the support used in this example was converted to H-form prior to deposition of gold, and it contained a small amount of sodium.

The catalyst was prepared according to Example 1, wherein 0.03 M aqueous $HAuCl_4$ solution was used as a source of gold. The support was prepared as described in Example 35. The catalyst was tested in CHHP decomposition as in Examples 36–39. The results of the test are shown in Table 2.

COMPARATIVE EXAMPLE 46

This comparative example illustrates using $Au/SiO_2$ catalyst in CHHP decomposition.

$Au/SiO_2$ catalyst was prepared according to Example 33. The catalyst was tested in CHHP decomposition as in Examples 36–39. The results of the test are shown in Table 2.

COMPARATIVE EXAMPLE 47

The catalyst, $Au/Al_2O_3$ was prepared as described in U.S. Pat. No. 6,160,183 to Druliner et al. The catalyst was tested in CHHP decomposition as in Examples 36–39. The results of the test are shown in Table 2.

As evidenced by Examples 36–47, gold supported on a porous crystalline silicate according to the present invention has significantly higher selectivity and stability in the process of CHHP decomposition to KA oil than gold supported on crystalline alumosilicates or other supports. Comparison of Examples 37 and 44 or 45 shows that removal of aluminum significantly improves the stability of the catalyst performance.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

TABLE 1

Cyclohexane oxidation with oxygen over Au/silicalite catalysts

| Example | Catalyst | Support structure | T, deg. C. | Cyclohexanone in reactor charge, g | Cyclohexane conversion, % | Selectivity to K + A + CHP % | Product distribution, % | | |
|---|---|---|---|---|---|---|---|---|---|
| | | | | | | | K | A | CHHP |
| 8 | $Au_{0.0046}$ $SiO_2$ | MFI | 170 | 0.7 | 3.39 | 91.4 | 52 | 45 | 4 |
| 9 | $Au_{0.0046}$ $SiO_2$ | MFI | 150 | 0 | 2.93 | 95.9 | 17.3 | 34.3 | 49.4 |
| 10 | $Au_{0.0046}$ $SiO_2$ | MFI | 150 | 0 | 6.09 | 88.0 | 22.4 | 43.4 | 34.2 |
| 11 | $Au_{0.0057}$ $(TiO_2)_{0.025}(SiO_2)$ | MFI | 170 | 0.7 | 3.20 | 92.0 | 50 | 47 | 3 |
| 12 | $Au_{0.0057}$ $(TiO_2)_{0.025}(SiO_2)$ | MFI | 170 | 0.7 | 4.21 | 90.6 | 50 | 47 | 4 |
| 13 | $Au_{0.0057}$ $(TiO_2)_{0.025}(SiO_2)$ | MFI | 170 | 0.7 | 6.66 | 88.1 | 53 | 47 | 0 |
| 14 | $Au_{0.0057}$ $(TiO_2)_{0.025}(SiO_2)$ | MFI | 150 | 0 | 4.11 | 91.2 | 28.5 | 52.4 | 19.1 |
| 15 | $Au_{0.0053}$ $(B_2O_3)_{0.0083}(SiO_2)$. | MFI | 170 | 0.7 | 2.53 | 90.3 | 38 | 45 | 16 |
| 16 | $Au_{0.0053}$ $(B_2O_3)_{0.0083}(SiO_2)$. | MFI | 170 | 0.7 | 3.11 | 86.6 | 34 | 51 | 15 |
| 17 | $Au_{0.0053}$ $(B_2O_3)_{0.0083}(SiO_2)$. | MFI | 170 | 0.7 | 4.88 | 87.9 | 46 | 48 | 6 |
| 18 | $Au_{0.024}$ $Al_2O_3 \cdot P_2O_5$ | ATS | 170 | 0.7 | 2.9 | 87 | 28 | 55 | 17 |
| 19 | $Au_{0.004}$ $(Na_2O)_{0.0025}(Al_2O_3)_{0.023}$ $SiO_2$ | FAU | 170 | 0.7 | 2.6 | 85 | 32.2 | 62.5 | 5.3 |
| 20 | No | | 170 | 0 | 1.63 | 87.3 | 7 | 11 | 8 |
| 21 | No | | 170 | 0 | 4.77 | 87.9 | 14 | 27 | 59 |
| 22 | No | | 170 | 0 | 7.35 | 81.5 | 20 | 44 | 36 |
| 23 | No | | 170 | 0.7 | 2.76 | 87.5 | 14 | 29 | 57 |
| 24 | No | | 170 | 0.7 | 3.68 | 84.5 | 16 | 41 | 43 |
| 25 | No | | 170 | 0.7 | 4.94 | 83.0 | 19 | 55 | 26 |
| 26 | No | | 170 | 0.7 | 6.32 | 80.2 | 23 | 57 | 21 |
| 27 | No | | 150 | 0 | 3.56 | 96.6 | 8.2 | 14.9 | 77.0 |
| 28 | No | | 150 | 0 | 8.45 | 88.4 | 14.8 | 27.1 | 58.1 |
| 29 | $(B_2O_3)_{0.0083}(SiO_2)$. | MFI | 170 | 0.7 | 2.78 | 87.3 | 15 | 36 | 49 |
| 30 | $SiO_2$ | MFI | 170 | 0.7 | 3.7 | 88 | 8 | 44 | 48 |
| 31 | $(TiO_2)_{0.025}(SiO_2)$ | MFI | 170 | 0.7 | 3.7 | 86 | 11 | 43 | 46 |
| 32 | $Al_2O_3 \cdot P_2O_5$ | ATS | 170 | 0.7 | 3.2 | 85.4 | 10 | 43 | 48 |
| 33 | $Au_{0.0045}$ $SiO_2$ | amorphous | 170 | 0.7 | 3.19 | 89.4 | 19 | 32 | 48 |
| 34 | $Au_{0.0043}$ $Al_2O_3$ | Boehmite | 170 | 0.7 | 2.56 | 87.7 | 7 | 31 | 62 |
| 35 | $Au_{0.0045}$ $(Na_2O)_{0.026}(Al_2O_3)_{0.15}SiO_2$ | FAU | 170 | 0.7 | 3.98 | 83 | 27 | 55 | 18 |

TABLE 2

CHHP decomposition over Au/silicalite catalysts

| | | | Averaged for 180 min | | |
|---|---|---|---|---|---|
| Example | Catalyst | Support structure | CHHP conversion (X), mol. % | CHHP selectivity for Ketone and alcohol, mol. % | Deactivation parameter, X(180 min)/X(60 min) |
| 36 | $Au_{0.0046}$ $SiO_2$ | MFI | 98 | 100 | 0.98 |
| 37 | $Au_{0.004}(Na_2O)_{0.0025}(Al_2O_3)_{0.023}$ $SiO_2$ | FAU | 98 | 63 | 0.99 |
| 38 | $Au_{0.005}(Na_2O)_{0.00007}(Al_2O_3)_{0.0086}$ $SiO_2$ | MFI | 96 | 91 | 0.92 |
| 39 | $Au_{0.0043}$ $(Na_2O)_{0.0086}(Al_2O_3)_{0.0086}$ $SiO_2$ | MFI | 97 | 94 | 0.91 |
| 40 | No | | 2.3 | 72 | — |
| 41 | $SiO_2$ | MFI | 11 | 83 | 0.97 |
| 42 | $(Na_2O)_{0.0086}(Al_2O_3)_{0.0086}SiO_2$ | MFI | 20 | 83 | 0.8 |
| 43 | $(Na_2O)_{0.00007}(Al_2O_3)_{0.0086}SiO_2$ | MFI | 52 | 66 | 1.0 |
| 44 | $Au_{0.005}(Na_2O)_{0.15}(Al_2O_3)_{0.15}SiO_2$ | FAU | 90 | 73 | 0.8 |
| 45 | $Au_{0.0045}(Na_2O)_{0.15}(Al_2O_3)_{0.15}SiO_2$ | FAU | 87 | 75 | 0.8 |
| 46 | $Au_{0.0045}$ $SiO_2$ | amorphous | 27 | 83 | 1.0 |
| 47 | $Au_{0.005}$ $Al_2O_3$ | boehmite | 95 | 93 | 0.8 |

What is claimed is:

1. A method of oxidizing a cycloalkane in a reaction mixture to form a product mixture containing a corresponding alcohol and ketone, the method comprising contacting the reaction mixture with a source of oxygen in the presence of a catalytic effective amount of gold supported on a porous crystalline silicate containing less than about 2 wt. % aluminum or a crystalline phosphate wherein the support comprises a three-dimensional framework with cavities and channels.

2. The method of claim 1 wherein the cycloalkane is cyclohexane.

3. A method for decomposing a cycloalkyl hydroperoxide in a reaction mixture to form a product mixture containing a corresponding alcohol and ketone, the method comprising contacting the reaction mixture with a catalytic effective amount of gold supported on a porous crystalline silicate or phosphate wherein the support comprises a three-dimensional framework with cavities and channels.

4. The method of claim 3 wherein the cycloalkyl hydroperoxide is cyclohexyl hydroperoxide.

5. The method of claim 1 or claim 3 wherein the porous crystalline silicate or crystalline phosphate support comprises a heteroatom.

6. The method of claim 5 wherein the porous crystalline silicate support has a structure selected from the group consisting of BEA, FAU, MFI, MEL, MOR, MTW, MTT, MCM-22, MCM-41, MCM-48, NU-1.

7. The method of claim 5 wherein the porous crystalline phosphate support has a structure selected from the group consisting of AFI, AEL, AFO, AFR, AFS, AFT, AFY, ATN, ATO, ATS, ATT, ATV, AWW.

8. The method of claim 1 or 3 wherein the crystalline silicate support is dealuminated zeolite having a structure selected from the group consisting of AFI, AEL, AFO, AFR, AFS, AFT, AFY, ATN, ATO, ATS, ATT, ATV, AWW.

9. The method of claim 5 wherein said heteroatom is selected from the group consisting of at least one element of Periods 2, 3, 4 and 5 except for aluminum and mixtures thereof.

10. The method of claim 6 wherein the porous crystalline silicate support has an MFI structure.

11. The method of claim 6 wherein the porous crystalline silicate support is titanosilicalite having an MFI structure.

12. The method of claim 6 wherein the porous crystalline silicate support is borosilicate having an MFI structure.

13. The method of claim 3 wherein the porous crystalline silicate support has an FAU structure.

14. The method of claim 4 wherein the porous crystalline phosphate support has an ATS structure.

15. The method of claim 1 or claim 3 wherein the porous crystalline silicate contains less than about 1 wt. % aluminum.

16. A method of oxidizing a cycloalkane in a reaction mixture to form a product mixture containing a corresponding alcohol and ketone, the method comprising contacting the reaction mixture with a source of oxygen in the presence of a catalytic effective amount of gold supported on a zeolite support containing less than about 1 wt. % aluminum.

17. The method of claim 16 wherein the cycloalkane is cyclohexane.

18. A method for decomposing a cycloalkyl hydroperoxide in a reaction mixture to form a product mixture containing a corresponding alcohol and ketone, the method comprising contacting the reaction mixture with a catalytic effective amount of gold supported zeolite support containing less than about 1 wt. % aluminum.

19. The method of claim 18 wherein the cycloalkyl hydroperoxide is cyclohexyl hydroperoxide.

20. The method of claim 16 or claim 18 wherein the support has a structure selected from the group consisting of BEA, FAU, MFI, MEL, MOR, MTW, MTT, MCM-22, MCM-41, MCM-48, NU-1.

21. The method of claim 16 or 18 wherein the support is dealuminated zeolite having a structure selected from the group consisting of AFI, AEL, AFO, AFR, AFS, AFT, AFY, ATN, ATO, ATS, ATT, ATV, AWW.

22. The method of 16 or claim 18 wherein the support comprises a heteroatom.

23. The method of claim 22 wherein said heteroatom is selected from the group consisting of at least one element of Periods 2, 3, 4 and 5 except for aluminum and mixtures thereof.

24. The method of claim 20 wherein the support has an MFI structure.

25. The method of claim 20 wherein the support is titanosilicalite having an MFI structure.

26. The method of claim 20 wherein the support is borosilicate having an MFI structure.

27. The method of claim 18 wherein the support has an FAU structure.

* * * * *